United States Patent [19]

Aldrich et al.

[11] 4,322,417

[45] Mar. 30, 1982

[54] ANTIHYPERTENSIVE POLYFLUOROISOPROPYL TRICYCLIC CARBOSTYRILS

[75] Inventors: Paul E. Aldrich, Wilmington, Del.; Gilbert H. Berezin, West Chester, Pa.

[73] Assignee: E. I. Du Pont de Nemours and Company, Wilmington, Del.

[21] Appl. No.: 863,267

[22] Filed: Dec. 22, 1977

[51] Int. Cl.³ .................... A61K 31/38; C07D 271/16; C07D 229/20; C07D 281/02
[52] U.S. Cl. .................................. 424/246; 424/258; 544/32; 546/93; 260/330
[58] Field of Search ........................... 260/283 S, 330; 424/258, 246; 544/32; 546/93

[56] References Cited

U.S. PATENT DOCUMENTS 3,042,671 7/1962 Lombardino .................... 260/283 S
3,178,348 4/1965 Bickerton et al. ................... 546/157
4,058,612 11/1977 Neustadt ............................. 260/260

*Primary Examiner*—Jose Tovar
*Assistant Examiner*—W. B. Springer

[57] ABSTRACT

Polyfluorohydroxyisopropyl tricyclic carbostyrils, such as 2,3-dihydro-7-methyl-9-[2,2,2-trifluoro-1-hydroxy-1-(trifluoromethyl)ethyl]-5H-[1,4]thiazino[2,3,4-ij]-quinolin-5-one, useful as antihypertensive agents.

30 Claims, No Drawings

ANTIHYPERTENSIVE POLYFLUOROISOPROPYL TRICYCLIC CARBOSTYRILS

BACKGROUND OF THE INVENTION

This invention relates to polyfluoroisopropyl tricyclic carbostyril antihypertensives.

Allied Chemical Corporation, in British Pat. No. 1,029,048, discloses hexahalohydroxyisopropyl aryl derivatives as intermediates in the preparation of aromatic carboxylic acids.

Jones, E. S., in U.S. Pat. Nos. 3,405,177 and 3,541,152, discloses hexahalohydroxyisopropyl aromatic amines useful as intermediates in the preparation of azo dyestuffs, polyesters, polyamides, insecticides, plasticizers, and pharmaceuticals.

Gilbert, E. E., in U.S. Pat. No. 3,532,753, discloses aromatic amino derivatives of hexahaloacetone, useful as insecticides.

German OS No. 2,552,993 discloses compounds containing a ureido or isoureido function which have utility as antihypertensive agents.

Meyer, H., at al., in U.S. Pat. No. 3,907,807, discloses benzoquinolizine antihypertensive agents; the following compound is exemplary:

Many current antihypertensive agents produce unwanted side effects because of their undesirable mechanism of action. For example, a guanethidine is an adrenergic neurone blocker, mecamylamine is a ganglion blocker, phenoxybenzamine is an α-adrenergic receptor blocker, and reserpine is a catecholamine depletor. Each of these mechanisms of action is undesirable because of the serious side effects produced. The compounds of this invention appear to lower blood pressure by a desirable mechanism of action—direct peripheral vasodilation—and, therefore have a distinct advantage over the above undesirable acting antihypertensive agents.

Furthermore, these compounds do not appear to produce central nervous system effects such as those seen with clonidine and α-methyldopa administration.

SUMMARY OF THE INVENTION

According to this invention, there is provided compounds of the following formula, processes for their manufacture, pharmaceutical compositions containing them, and methods of using them to treat hypertension in mammals.

where
$R_1 = CF_3$ or $CF_2H$;
$R_2 = CF_3$, $CF_3H$ or $CF_2Cl$;
$R_3 = H$, acyl or alkyl of 1-6 carbon atoms;
$R_4 = $ methyl or ethyl;

$$X = -\underset{\underset{R_5}{|}}{CH}-CH_2- \text{ or } -\underset{\underset{R_5}{|}}{CH}-CH_2-CH_2-;$$

$R_5 = H$, methyl or ethyl; and pharmaceutically suitable salts, where $R_3 = H$.

Preferred for their high degree of activity are those compounds of Formula (1) where, independently:

(a) $R_1 = CF_3$ or $CHF_3$; and $R_2 = CF_3$; or
(b) $R_3 = H$; or
(c) $R_4 = $ methyl; or $$(d) \ X = -\underset{\underset{R_5}{|}}{CH}-CH_2- \text{ or}$$

(e) $R_5 = H$ or methyl.

Where $R_3$ is alkyl, a preferred definition is alkyl of 1-2 carbon atoms and more preferably 1 carbon atom.

The following compound is specifically preferred: 2,3-dihydro-7-methyl-9-[2,2,2-trifluoro-1-hydroxy-1-(trifluoromethyl)ethyl]-5H-[1,4]thiazino[2,3,4-ij]quinolin-5-one.

ACYL DERIVATIVES

Acyl derivatives of the hydroxy function of the compounds of this invention show excellent antihypertensive activity. The acyl derivatives (i.e., where $R_3$ is not hydrogen or alkyl) are hydrolyzed easily to the parent hydroxy compound ($R_3 = H$), and it is believed that their antihypertensive effect is due to a facile in vivo hydrolysis. Acylation can be used to give derivatives with a variety of different physical properties, but with little difference in biological properties from the parent hydroxy compound. It is concluded, therefore, that the range of acyl groups is practically unlimited and not critical for antihypertensive activity. Among the acyl groups that can be used are alkanoyl, alkenoyl, and aroyl.

SYNTHESIS

Polyfluorohydroxyisopropyl amines are prepared in the following manner:

Where $R_1$ and $R_2$ are as previously defined

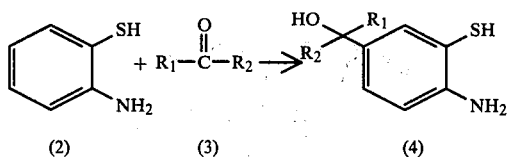

Compounds of the above type where $R_1=R_2=CF_3$ have been prepared by E. E. Gilbert, *J. Het. Chem.*, 6, 483 (1969). The procedure described utilizes the reaction of 2-aminomercaptobenzene (2) with a hydrate of hexafluoroacetone (3) to give an adduct such as (4). This procedure is preferred for most addition of fluoroacetones in this series. However, in some cases it may be preferable to react 2-amino-mercaptobezene with a fluoroacetone in the presence of a catalyst such as aluminum chloride.

1,4-Benzothiazines 1,4-Benzothiazine precursors unsubstituted in the 2- or 3-position or substituted in the 2-position with a methyl or ethyl group are prepared as follows:

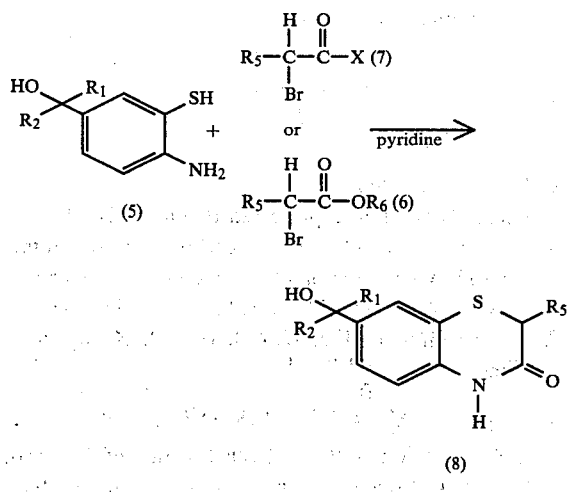

In the above scheme, $R_1$, $R_2$ and $R_5$ are as previously defined and $R_6$ is methyl or ethyl. If desired, (8) can be prepared by reaction of an α-haloacyl halide (7) with (5) in a solvent such as toluene in the presence of a base such as pyridine.

The preparation of (8) where $R_1=R_2=CF_3$ and $R_5=H$ has been described by E. E. Gilbert, *J. Het. Chem.*, 6, 483, (1969). Reduction of (8) with a reducing agent such as sodium bis(2-methoxyethoxy)-aluminum hydride or diborane give the precursor (9):

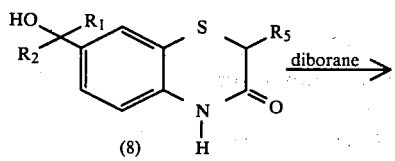

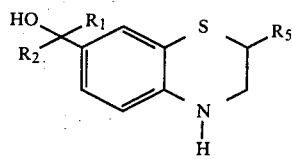

Intermediates such as (5) are used to prepare precursors as described in the following reaction schemes.

1,4-Benzothiazines 1,4-Benzothiazine precursors substituted with methyl or ethyl in the 3-position are prepared as follows:

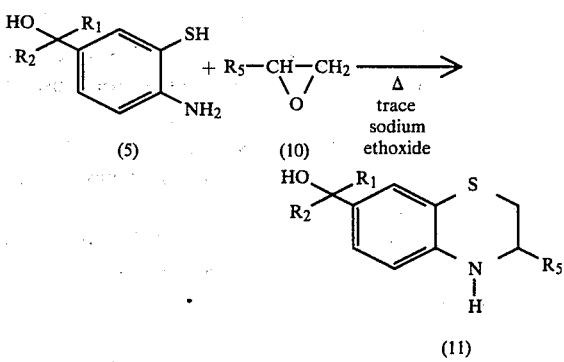

An alkylene oxide such as (10) can be added to (5) in a solvent such as ethanol that contains a trace of sodium ethoxide. An exothermic reaction results. The product can be isolated and distilled to give the precursor, (11).

1,5-Benzothiazepines 1,5-Benzothiazepine precursors unsubstituted in the 2 position or substituted in the 2-position with methyl or ethyl are prepared as follows:

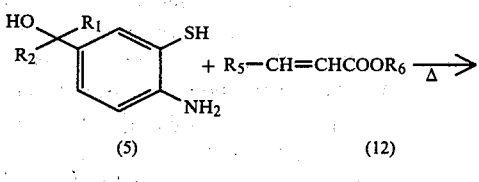

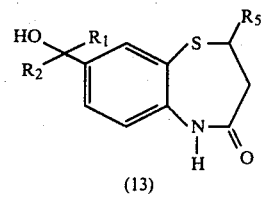

A substituted-acrylic acid or ester (12), ($R_5=H$, methyl or ethyl; $R_6=H$, methyl or ethyl), can be heated with (5) at 100° to 140° C. to give (13). Reduction of (13) with a reducing agent such as sodium bis(2-methoxyethoxy)-aluminum hydride or diborane gives the precursor (14).

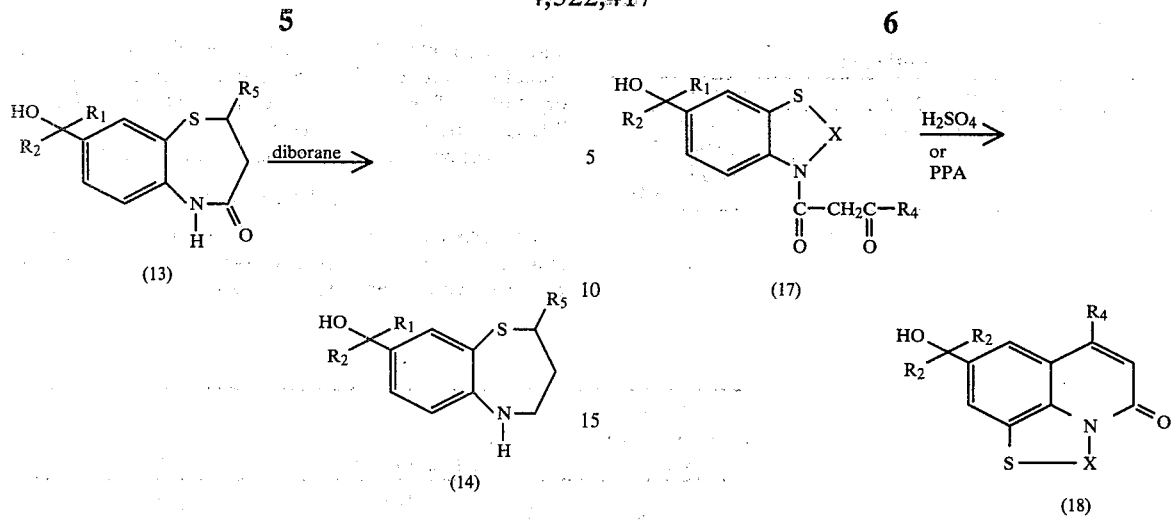

Intermediate Amides

Intermediate amides are prepared as shown in the following reaction:

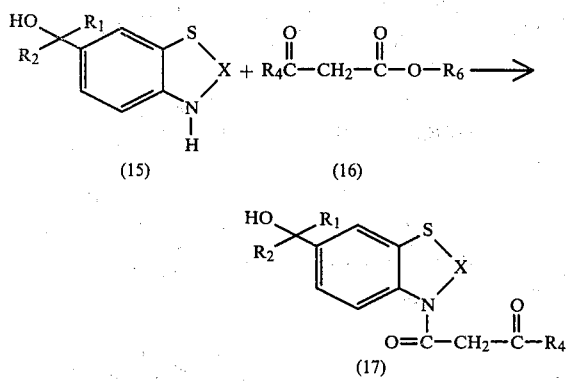

$R_1$ and $R_2$ are previously defined; $R_4$ = methyl or ethyl; $R_6$ = methyl or ethyl; X is as previously defined.

The amide (17) is prepared by heating equimolar amounts of amine (15) and ketoester (16) in an oil bath. The preferred temperature range is about 180°–220° C. Alternatively, the reactants can be refluxed together in a high-boiling solvent, for example, xylene.

The reaction can be conveniently followed by periodically removing a test portion and performing thin layer chromatographic analysis. When no further reaction is observed, the amide (17) can be isolated by crystallization and/or chromatography. Occasionally, purification is difficult and therefore, cyclization of the crude amide is more convenient.

When $R_4 = CH_3$, the amides (17) are prepared more conveniently and in better yield using diketene instead of the ketoester (16). A slight excess of diketene is added to the amide (15) dissolved in an inert solvent (for example, anhydrous tetrahydrofuran or toluene), and held at room temperature. If the reaction is slow (as indicated by thin layer chromatography), the mixture is heated until no further reaction is observed. The crude product is often satisfactory for cyclization in acid, but it can be purified by recrystallization and/or chromatography.

The cyclization products are prepared as shown by the following reaction:

Cyclization is accomplished by heating the amide (17) in a condensing agent such as sulfuric acid or polyphosphonic acid; usually heating in concentrated sulfuric acid at 70°–100° C., preferably 85°–90° C., for one to eighteen hours, preferably two to four hours, completes the reaction. Completion of the reaction can be conveniently checked by analyzing with thin layer chromatography. The product (18), is isolated by pouring the acid solution into excess ice water, removing the precipitated material by filtration, washing with water and drying. Further purification, if necessary, can be done by recrystallization and/or chromatography.

Esters (where $R_3$ = acyl) are prepared from (18) by reaction with acid chlorides or anhydrides with or without solvents. Because of the tertiary nature and high acidity of the alcohol group, esterification is rather slow at room temperature but can be greatly accelerated by using high boiling solvents (with or without the addition of a base) or using refluxing pyridine as a solvent and base.

Ethers are prepared from (18) by converting it to a salt by treating with a suitable base (for example, potassium tert-butoxide), then O-alkylating the salt by heating with a dialkyl sulfate or alkyl halide.

EXAMPLE 1

4-Amino-3-mercapto[2,2,2-trifluoro-1-hydroxy-1-(trifluoromethyl)ethyl]-benzene.

To 193 gm (1.0 mole) of hexafluoroacetone sesquihydrate is added 62.5 gm (0.5 mole) of 2-amino-mercaptobenzene. The solution is stirred and heated at reflux for 60 hours. At the end of this period, the solution is cooled and added to 1 liter of water. The resultant solid is filtered and recrystallized from chlorobutane to give 92.5 gm. of 4-amino-3-mercapto[2,2,2-trifluoro-1-hydroxy-1-(trifluoromethyl)ethyl]-benzene, m.p. 121°–123°.

EXAMPLES 2–3

The procedure of Example 1 can be used with the appropriate fluoroketone and 2-amino-mercaptobenzene to obtain the indicated product.

| Example No. | Fluoroketone | Product |
|---|---|---|
| 2. | $HCF_2-\underset{\underset{O}{\|\|}}{C}-CF_3$ |  |

| Example No. | Fluoroketone | Product |
|---|---|---|
| 3. | CF₂Cl—C(=O)—CF₃ | HO, CF₂Cl, CF₃ substituents on benzene with SH and NH₂ | and poured into 800 ml of ice-water. The resultant precipitate is filtered. The precipitate is air dried and recrystallized from ethyl acetate/hexane to give 14 gm of 7-[2,2,2-trifluoro-1-hydroxy-1-(trifluoromethyl)-ethyl]-2H-1,4-benzothiazin-3(4H)-one, m.p. 230°–232°.

EXAMPLES 6–11

The procedure of Example 5 can be used with the appropriate α-halo-ester and 4-amino-3-mercaptobenzene to give the indicated product.

| Example No. | 4-amino-3-mercapto-benzene | α-halo-ester | Product |
|---|---|---|---|
| 6 | HO, CF₃, CF₃ substituents; SH, NH₂ on benzene | CH₃—CHBr—C(=O)—OCH₃ | HO, CF₃, CF₃; fused benzothiazinone with 3-CH₃ |
| 7 | HO, CF₃, CF₃ substituents; SH, NH₂ on benzene | C₂H₅—CHBr—C(=O)—OC₂H₅ | HO, CF₃, CF₃; fused benzothiazinone with 3-C₂H₅ |
| 8 | HO, HCF₂, CF₃ substituents; SH, NH₂ on benzene | BrCH₂C(=O)—OC₂H₅ | HO, HCF₂, CF₃; fused benzothiazinone |
| 9 | HO, HCF₂, CF₃ substituents; SH, NH₂ on benzene | CH₃—CHBr—C(=O)—OC₂H₅ | HO, HCF₂, CF₃; fused benzothiazinone with 3-CH₃ |
| 10 | HO, HCF₂, HCF₂ substituents; SH, NH₂ on benzene | BrCH₂C(=O)—OC₂H₅ | HO, HCF₂, HCF₂; fused benzothiazinone |
| 11 | HO, CF₂Cl, CF₃ substituents; SH, NH₂ on benzene | BrCH₂C(=O)—OC₂H₅ | HO, CF₂Cl, CF₃; fused benzothiazinone |

EXAMPLE 4

4-Amino-3-mercapto[2,2-difluoro-1-hydroxy-1-(difluoromethyl)ethyl]-benzene.

A mixture of 2-amino-mercaptobenzene, toluene and symtetrafluoroacetone can be heated in a Hastelloy ® bomb. The solvent can be removed by evaporation and the residual material can be purified by chromatography on silica gel to give 4-amino-3-mercapto[2,2-difluoro-1-hydroxy-1-(difluoromethyl)-ethyl]-benzene.

EXAMPLE 5

7-[2,2,2-Trifluoro-1-hydroxy-1-(trifluoromethyl)ethyl]-2H-1,4-benzothiazin-3(4H)-one To 140 ml. of ethylene glycol is added 24 gm (0.08 mole) of 4-amino-3-mercapto[2,2,2-trifluoro-1-hydroxy-1-(trifluoromethyl)ethyl]-benzene, 14 gm. (0.08 mole) ethyl bromoacetate, and 6.4 gm. (0.08 mole) of pyridine. The solution is stirred and heated at 105°–110° for 8 hours. At the end of this period the solution is cooled

EXAMPLE 12

2,3-Dihydro-8-[2,2,2-trifluoro-1-hydroxy-1-(trifluoromethyl)ethyl]-1,5-benzothiazepin-4(5H)-one To 4-amino-3-mercapto[2,2,2-trifluoro-1-hydroxy-1-(trifluoromethyl)ethyl]benzene is added acrylic acid. The reaction mixture can be heated in a nitrogen atmosphere until analysis by thin layer chromatography indicates the reaction to complete. The residual material can be chromatographed and recrystallized to give 2,3-dihydro-8-[2,2,2-trifluoro-1-hydroxy-1-(trifluoromethyl)ethyl]1,5-benzothiazepin-4(5H)-one

EXAMPLES 13–17

The procedure of Example 12 can be used with the appropriate 4-amino-3-mercaptobenzene and olefinic acid to give the indicated product.

| Example No. | 4-Amino-3-Mercaptobenzene | Olefinic Acid | Product |
|---|---|---|---|
| 13. | HO-C(CF₃)₂ substituted benzene with SH and NH₂ | CH₃CH=CHCOOH | benzothiazepinone with CH₃ |
| 14. | HO-C(CF₃)₂ substituted benzene with SH and NH₂ | CH₃CH₂CH=CHCOOH | benzothiazepinone with CH₂CH₃ |
| 15. | HO-C(CF₃)(HCF₂) substituted benzene with SH and NH₂ | CH₂=CH—COOH | benzothiazepinone |
| 16. | HO-C(CF₃)(ClCF₂) substituted benzene with SH and NH₂ | CH₂=CH—COOH | benzothiazepinone |
| 17. | HO-C(CF₂)(HCF₂) substituted benzene with SH and NH₂ | CH₂=CH—COOH | benzothiazepinone |

EXAMPLE 18

3,4-Dihydro-7-[2,2,2-trifluoro-1-hydroxy-1-(trifluoromethyl)ethyl]-2H-1,4-benzothiazine To 300 ml of 1M-borane-tetrahydrofuran complex is added a solution of 66 gm. (0.2 mole) of 7-[2,2,2-trifluoro-1-hydroxy-1-(trifluoromethyl)ethyl]-2H-1,4-benzothiazin-3(4H)-one in 300 ml anhydrous tetrahydrofuran at a rate such that the temperature rises slowly to 40°. When the addition is complete the solution is heated at reflux and stirred for 18 hours. At the end of this period, the solution is cooled and 19 ml. of concentrated hydrochloric acid is added cautiously. The resultant solution is concentrated at reduced pressure. The residual oil is treated with 300 ml of water and the mixture is extracted with ether. The ethereal solution is extracted with 5% sodium bicarbonate solution and dried with anhydrous magnesium sulfate. The ethereal solution is filtered and concentrated to give a solid. The solid is recrystallized from hexane to give 40 gm. of 3,4-dihydro-7-[2,2,2-trifluoro-1-hydroxy-1-(trifluoromethyl)ethyl]-2H-1,4-benzothiazine, m.p. 99°–100°.

EXAMPLES 19–28

The procedure of Example 18 can be used with the appropriate lactam to give the indicated product.

| Example No. | Lactam | Product |
|---|---|---|
| 19. | HO-C(CF₃)₂ benzothiazinone with CH₃ | HO-C(CF₃)₂ benzothiazine with CH₃ |
| 20. | HO-C(CF₃)₂ benzothiazinone with C₂H₅ | HO-C(CF₃)₂ benzothiazine with C₂H₅ |
| 21. | HO-C(CF₃)(HCF₂) benzothiazinone | HO-C(CF₃)(HCF₂) benzothiazine |

-continued

| Example No. | Lactam | Product |
|---|---|---|
| 22. | 7-[HO,CF3,ClCF2]-benzothiazine, 3-CH3, lactam | corresponding dihydrobenzothiazine |
| 23. | 7-[HO,HCF2,HCF2]-benzothiazine, 3-C2H5, lactam | corresponding dihydrobenzothiazine |
| 24. | 7-[HO,CF3,CF3]-benzothiazepine lactam | corresponding dihydrobenzothiazepine |
| 25. | 7-[HO,CF3,CF3]-benzothiazepine, CH3-substituted lactam | corresponding dihydrobenzothiazepine |
| 26. | 7-[HO,CF3,HCF2]-benzothiazepine lactam | corresponding dihydrobenzothiazepine |
| 27. | 7-[HO,HCF2,HCF2]-benzothiazepine, C2H5-substituted lactam | corresponding dihydrobenzothiazepine |
| 28. | 7-[HO,CF3,ClCF2]-benzothiazepine, C2H5-substituted lactam | corresponding dihydrobenzothiazepine |

EXAMPLE 29

3,4-Dihydro-3-methyl-7-[2,2,2-trifluoro-1-hydroxy-1-(trifluoromethyl)ethyl]-2H-1,4-benzothiazine To a solution of 4-amino-3-mercapto[2,2,2-trifluoro-1-hydroxy-1-(trifluoromethyl)ethyl]-benzene in ethanol containing a trace of sodium ethoxide can be added propylene oxide to the cold solution. An exothermic reaction occurs. When reaction subsides, the solution is heated on the steam bath. The product can be isolated and distilled to give 3,4-dihydro-3-methyl-7-[2,2,2-trifluoro-1-hydroxy-1-(trifluoromethyl)ethyl]-2H-1,4-benzothiazine.

EXAMPLES 30–32

The procedure of Example 29 can be used with the appropriate 4-amino-3-mercaptobenzene with the appropriate alkylene oxide to give the indicated product.

| Example No. | 4-Amino-3-Mercaptobenzene | Alkylene oxide | Product |
|---|---|---|---|
| 30. | HO,CF3,CF3-substituted 2-SH-aniline | CH3CH2CHCH2-O (1,2-epoxybutane) | 3-C2H5-benzothiazine with HO,CF3,CF3 substituent |
| 31. | HO,CF3,HCF2-substituted 2-SH-aniline | CH3CH—CH2-O (propylene oxide) | 3-CH3-benzothiazine with HO,CF3,HCF2 substituent |

| Example No. | 4-Amino-3-Mercaptobenzene | Alkylene oxide | Product |
|---|---|---|---|
| 32. | HO-C(HCF₂)(HCF₂)-C₆H₃(SH)(NH₂) | CH₃CH—CH₂ (epoxide) | HO-C(HCF₂)(HCF₂)-benzothiazine-CH₃ |

EXAMPLE 33

2,3-Dihydro-7-methyl-9-[2,2,2-trifluoro-1-hydroxy-1-(trifluoromethyl)ethyl]-5H-1,4-thiazino[2,3,4-ij]-quinolin-5-one To a solution of 10 gm. (0.032 mole) of 3,4-dihydro-7-[2,2,2-trifluoro-1-hydroxy-1-(trifluoromethyl)ethyl]-2H-1,4-benzothiazine in 150 ml. of anhydrous toluene is added 3 gm. (0.035 mole) of diketene. The solution is stirred and heated at reflux in a nitrogen atmosphere for 24 hours. At the end of this period an additional 2 gm. of diketene is added and heating and stirring is continued for an additional 24 hours. At the end of this period, the solution is cooled, and 3,4-dihydro-1-(1,3-dioxobutyl)-7-[2,2,2-trifluoro-1-hydroxy-1-(trifluoromethyl)ethyl]-2H-1,4-benzothiazine, m.p. 162°–164° is precipitated.

To 9 ml. of concentrated sulfuric acid is added 4.5 gm. (0.01 mole) of 3,4-dihydro-1-(1,3-dioxobutyl)-7-[2,2,2-trifluoro-1-hydroxy-1-(trifluoromethyl)ethyl]-2H-1,4-benzothiazine. The solution is stirred and heated at 90° for five hours. At one end of this period, the solution is added to water. The resultant precipitate is filtered, washed with water, and air dried. The solid is recrystallized from ethyl acetate/hexane to give 2.1 gm. of 2,3-dihydro-7-methyl-9-[2,2,2-trifluoro-1-hydroxy-1-(trifluoromethyl)ethyl]-5H-1,4-thiazino[2,3,4-ij]-quinolin-5-one, m.p. 227°–229°.

EXAMPLES 34–41

The procedure of Example 33 can be used with diketene and the appropriate precursor to give the indicated product.

| Example No. | Precursor | Product |
|---|---|---|
| 34. | HO-C(CF₃)(CF₃)-benzothiazine-3-CH₃ | HO-C(CF₃)(CF₃)-thiazino-quinolinone-CH₃ |
| 35. | HO-C(CF₃)(CF₃)-benzothiazine-3-CH₃ (N-H) | HO-C(CF₃)(CF₃)-thiazino-quinolinone-CH₃ (CH₃) |
| 36. | HO-C(CF₃)(CF₃)-benzothiazine-C₂H₅ | HO-C(CF₃)(CF₃)-thiazino-quinolinone-C₂H₅ |
| 37. | HO-C(HCF₂)(CF₃)-benzothiazine | HO-C(HCF₂)(CF₃)-thiazino-quinolinone-CH₃ |
| 38. | HO-C(HCF₂)(CF₃)-benzothiazine-CH₃ | HO-C(HCF₂)(CF₃)-thiazino-quinolinone-CH₃-CH₃ |
| 39. | HO-C(ClCF₂)(CF₃)-benzothiazine | HO-C(CF₂Cl)(CF₃)-thiazino-quinolinone-CH₃ |
| 40. | HO-C(CF₃)(CF₃)-benzothiazepine | HO-C(CF₃)(CF₃)-thiazino-quinolinone-CH₃ (7-membered) |
| 41. | HO-C(HCF₂)(CF₃)-benzothiazepine-CH₃ | HO-C(HCF₃)(CF₃)-thiazino-quinolinone-CH₃-CH₃ |

EXAMPLE 42

2,3-Dihydro-7-ethyl-9-[2,2,2-trifluoro-1-hydroxy-1(trifluoromethyl)ethyl]-5H-1,4-thiazino-[2,3,4-ij]-quinolin-5-one A stirred mixture of 3,4-dihydro-7-[2,2,2-trifluoro-1-hydroxy-1-(trifluoromethyl)ethyl]-2H-1,4-benzothiazine and ethyl propionylacetate can be heated in an oil bath to give 3,4-dihydro-1-(1,3-dioxopentyl)-7-[2,2,2- trifluoro-1-hydroxy-1-(trifluoromethyl)ethyl]-2H-1,4-benzothiazine.

A solution of 3,4-dihydro-1-(1,3-dioxopentyl)-[2,2,2-trifluoro-1-hydroxy-1-(trifluoromethyl)ethyl]-2H-1,4-benzothiazine in concentrated sufluric acid can be heated until analysis by thin layer chromatography indicates the reaction to be complete. The solution can be poured into ice water, isolated and purified to give 2,3-dihydro-7-ethyl-9-[2,2,2-trifluoro-1-hydroxy-1-(trifluoromethyl)ethyl]-5H-1,4-thiazino-[2,3,4-ij]-quinolin-5-one.

EXAMPLES 43–47

The procedure of Example 42 can be used with the appropriate precursor and ethyl propionylacetate to give the indicated product

| Ex. No. | Precursor | Product |
|---|---|---|
| 44. | HO-C(CF₃)₂-[benzothiazine]-CH₃ | HO-C(CF₃)₂-[thiazinoquinolinone]-C₂H₅, CH₃ on S-CH |
| 45. | HO-C(HCF₂)(CF₃)-[benzothiazine] | HO-C(HCF₂)(CF₃)-[thiazinoquinolinone]-C₂H₅ |
| 46. | HO-C(CF₃)₂-[benzothiazepine] | HO-C(CF₃)₂-[thiazinoquinolinone]-C₂H₅ |
| 47. | HO-C(HCF₂)₂-[benzothiazepine] | HO-C(HCF₂)₂-[thiazinoquinolinone]-C₂H₅ |

EXAMPLE 48

2,3-Dihydro-7-methyl-9-[2,2,2-trifluoro-1-hydroxy-1-(trifluoromethyl)ethyl]-5H-1,4-thiazino-[2,3,4-ij]-quinolin-5-one Acetate To a solution of 2,3-dihydro-7-methyl-9-[2,2,2-trifluoro-1-hydroxy-1-(trifluoromethyl)ethyl]-5H-1,4-thiazino[2,3,4-ij]-quinolin-5-one in dry pyridine can be added acetyl chloride. The solution is heated at reflux, and when the reaction is complete, the solution can be poured into cold 1 N hydrochloric acid solution, extracted, isolated and purified to give 2,3-dihydro-7-methyl-9-[2,2,2-trifluoro-1-hydroxy-1-(trifluoromethyl)ethyl]-5H-1,4-thiazino-[2,3,4-ij]-quinolin-5-one acetate.

EXAMPLES 49–52

The procedure of Example 48 can be used with the appropriate acyl halide to give the indicated products.

| Ex. No. | Acyl Halide | Products |
|---|---|---|
| 49. | CH₃CH₃C(=O)—Cl | CH₃CH₂C(=O)—O—C(CF₃)₂—[thiazinoquinolinone]-CH₃ |
| 50. | Ph—C(=O)—Cl | Ph—C(=O)—O—C(CF₃)₂—[thiazinoquinolinone]-CH₃ |
| 51. | CH₃(CH₂)₄C(=O)—Cl | CH₃(CH₂)₄—C(=O)—O—C(CF₃)₂—[thiazinoquinolinone]-CH₃ |
| 52. | CH₃—CH=CH—C(=O)—Cl | CH₃—CH=CH—C(=O)—O—C(CF₃)₂—[thiazinoquinolinone]-CH₃ |

EXAMPLE 43

2,3-Dihydro-7-methyl-9-[2,2,2-trifluoro-1-methoxy 1-(trifluoromethyl)ethyl]-5H-1,4-thiazino-[2,3,4-ij]-quinolin-5-one.

To a solution of 2,3-dihydro-7-methyl-9-[2,2,2-trifluoro-1-hydroxy-1-(trifluoromethyl)ethyl]-5H-1,4-thiazino-[2,3,4-ij]-quinolin-5-one in dimethyl formamide can be added sodium hydride and dimethyl sulfate. The mixture can be stirred and heated in a nitrogen atmosphere until the reaction is complete, treated with ethanol and purified to give 2,3-dihydro-7-methyl-9-[2,2,2-trifluoro-1-methoxy-1-(trifluoromethyl)ethyl]-5H-1,4-thiazino-[2,3,4-ij]-quinolin-5-one.

EXAMPLES 54–55

The procedure of Example 53 can be used with the appropriate alkyl sulfate or halide and a base such as sodium hydride, potassium t-butoxide or potassium carbonate to give the indicated product.

| Ex. No. | Alkyl Sulfate or Alkyl Halide | Product |
| --- | --- | --- |
| 54. | $(C_2H_5)_2SO_4$ | $C_2H_5O$-substituted product |
| 55. | $CH_3(CH_2)_5-I$ | $CH_3(CH_2)_5O$-substituted product |

In the above examples all parts are by weight and all temperatures are in degrees centigrade, unless otherwise specified.

DOSAGE FORMS

The compounds of this invention can be administered in the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively or concurrently, administration can be by the oral route.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1 to 50 milligrams per kilogram of body weight. Ordinarily, from 0.5 to 40, and preferably 1.0 to 20, milligrams per kilogram per day in one or more applications per day is effective to obtain desired results. For the more potent compounds of the invention, e.g. 2,3-dihydro-7-methyl-9-[2,2,2-trifluoro-1-hydroxy-1-(trifluoromethyl)ethyl]-5H-[1,4]thiazino[2,3,4-ij]quinolin-5-one, the daily dosage ranges are from about 0.1 to 10 mg/kg, preferably 0.5 to 5 mg/kg, and more preferably 0.5 to 5 mg/kg.

Dosage forms (compositions) suitable for internal administration contain from about 0.1 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

CAPSULES

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by filtration.

SUSPENSION

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

INJECTABLE

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

The antihypertensive activity of the compounds of this invention is evidenced by tests conducted in hypertensive rats. In these tests rats are made hypertensive by subcutaneous implantation of pellets of desoxycorticosterone acetate (DOCA) and by giving the rats saline solution to drink essentially according to the method described by Sturtevant [Annals of Internal Medicine, 49, 1281 (1958)]. Graded dose levels of each compound are administered orally to groups of 8 hypertensive rats. The compound is prepared in an aqueous polyvinyl alcohol/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by modification of the microphone-manometer technique [(Friedman, M. and Freed, S. C., Proc. Soc. Exp. Biol. and Med., 70, 670 (1949)]. That dose of compound which produces a 30 mm mercury (mm Hg) reduction in blood pressure when compared to the mean systolic arterial blood pressure of the control animals is then determined (Effective Dose 30). For example, an ED30 of 2.9 mg/kg orally was obtained with 2,3-dihydro-7-methyl-9-[2,2,2-trifluoro-1-hydroxy-1-(trifluoromethyl)ethyl]-5H-[1,4]thiazino[2,3,4-ij]quinolin-5-one.

"Consisting essentially of" is intended to have its customary meaning: namely; that all specified materials and conditions are very important in practicing the invention but that unspecified materials and conditions are not excluded so long as they do not prevent the benefits of the invention from being realized.

What is claimed is:
1. A compound of the formula

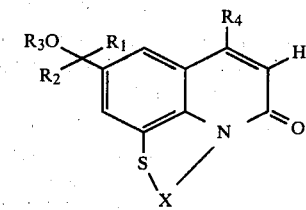

where
$R_1 = CF_3$ or $CF_2H$;
$R_2 = CF_3$, $CF_2H$ or $CF_2Cl$;
$R_3 = H$, acyl selected from alkanoyl, alkenoyl or hydrocarbon aroyl or alkyl of 1–6 carbon atoms;
$R_4 = $ methyl or ethyl;

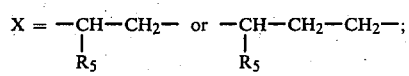

$R_5 = H$, methyl or ethyl; and pharmaceutically suitable salts, when $R_3 = H$.

2. A compound of claim 1 where $R_1 = CF_3$ or $CHF_2$ and $R_2 = CF_3$.

3. A compound of claim 1 where $R_3 = H$.

4. A compound of claim 1 where $R_4 = $ methyl.

5. A compound of claim 1 where

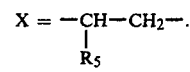

6. A compound of claim 1 where $R_5 = H$ or methyl.

7. A compound of claim 1 where
$R_1 = CF_3$ or $CHF_2$;
$R_2 = CF_3$;
$R_3 = H$;
$R_4 = $ methyl;

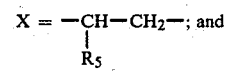

$R_5 = H$ or methyl.

8. A compound of claim 1 where $R_3$ is alkyl of 1–2 carbon atoms.

9. A compound of claim 8 where $R_3$ is methyl.

10. The compound of claim 1 which is 2,3-dihydro-7-methyl-9-[2,2,2-trifluoro-1-hydroxy-1-(trifluoromethyl)ethyl]5H-[1,4]thiazino[2,3,4-ij]quinolin-5-one.

11. A pharmaceutical composition consisting essentially of a pharmaceutically suitable carrier and an effective anti-hypertensive amount of a compound of claim 1.

12. A pharmaceutical composition consisting essentially of a pharmaceutically suitable carrier and an effective anti-hypertensive amount of a compound of claim 2.

13. A pharmaceutical composition consisting essentially of a pharmaceutically suitable carrier and an effective anti-hypertensive amount of a compound of claim 3.

14. A pharmaceutical composition consisting essentially of a pharmaceutically suitable carrier and an effective anti-hypertensive amount of a compound of claim 4.

15. A pharmaceutical composition consisting essentially of a pharmaceutically suitable carrier and an effective anti-hypertensive amount of a compound of claim 5.

16. A pharmaceutical composition consisting essentially of a pharmaceutically suitable carrier and an effective anti-hypertensive amount of a compound of claim 6.

17. A pharmaceutical composition consisting essentially of a pharmaceutically suitable carrier and an effective anti-hypertensive amount of a compound of claim 7.

18. A pharmaceutical composition consisting essentially of a pharmaceutically suitable carrier and an effective anti-hypertensive amount of a compound of claim 8.

19. A pharmaceutical composition consisting essentially of a pharmaceutically suitable carrier and an effective anti-hypertensive amount of a compound of claim 9.

20. A pharmaceutical composition consisting essentially of a pharmaceutically suitable carrier and an effective anti-hypertensive amount of the compound of claim 10.

21. A method of treating hypertension in a mammal which comprises administering to a mammal an effective antihypertensive amount of a compound of claim 1.

22. A method of treating hypertension in a mammal which comprises administering to a mammal an effective antihypertensive amount of a compound of claim 2.

23. A method of treating hypertension in a mammal which comprises administering to a mammal an effective antihypertensive amount of a compound of claim 3.

24. A method of treating hypertension in a mammal which comprises administering to a mammal an effective antihypertensive amount of a compound of claim 4.

25. A method of treating hypertension in a mammal which comprises administering to a mammal an effective antihypertensive amount of a compound of claim 5.

26. A method of treating hypertenion in a mammal which comrpises administering to a mammal an effective antihypertensive amount of a compound of claim 6.

27. A method of treating hypertension in a mammal which comprises to administering to a mammal an effective antihypertensive amount of a compound of claim 7.

28. A method of treating hypertension in a mammal which comprises administering to a mammal an effective antihypertensive amount of a compound of claim 8.

29. A method of treating hypertension in a mammal which comprises to administering to a mammal an effective antihypertensive amount of a compound of claim 9.

30. A method of treating hypertension in a mammal which comprises to administering to a mammal an effective antihypertensive amount of a compound of claim 10.

* * * * *